United States Patent

Teraji et al.

[11] Patent Number: 4,481,196
[45] Date of Patent: Nov. 6, 1984

[54] GLYCOSIDE PHOSPHATE DERIVATIVES, PHARMACEUTICAL COMPOSITION OF THE SAME AND METHOD OF USE

[75] Inventors: Tsutomu Teraji, Osaka; Eishiro Todo; Norihiko Shimazaki, both of Toyonaka; Teruo Oku, Osaka; Takayuki Namiki, Minoo, all of Japan

[73] Assignee: Fujisawa Pharmaceutical Co., Ltd., Osaka, Japan

[21] Appl. No.: 528,062

[22] Filed: Aug. 31, 1983

[51] Int. Cl.³ ............... A61K 31/70; C07H 9/140; C07H 15/02
[52] U.S. Cl. ................... 424/180; 536/4.1; 536/17.2; 536/18.7; 536/55.3; 536/117
[58] Field of Search .......... 536/117, 18.7, 55.3, 536/4.1, 17.2; 424/180

[56] References Cited

U.S. PATENT DOCUMENTS 3,524,846 8/1970 Moffatt et al. ............... 536/117

OTHER PUBLICATIONS

Migrdichian, Organic Synthesis, vol. 1, pp. 157–158 (1957).

Primary Examiner—Johnnie R. Brown
Assistant Examiner—Elli Peseler
Attorney, Agent, or Firm—Oblon, Fisher, Spivak, McClelland & Maier

[57] ABSTRACT

New phosphate derivatives represented by the formula:

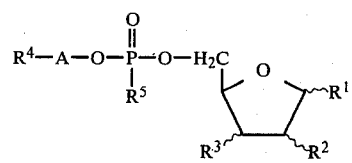

wherein
$R^1$, $R^2$, and $R^3$ are each hydroxy, alkoxy, alkanoylamino or protected hydroxy;
A is lower alkylene;
$R^4$ is alkylammonio, cyclic ammonio or cyclic amino; and
$R^5$ is oxido anion or hydroxy;
and pharmaceutically acceptable salt thereof, which exhibit antitumor activity.

19 Claims, No Drawings

GLYCOSIDE PHOSPHATE DERIVATIVES, PHARMACEUTICAL COMPOSITION OF THE SAME AND METHOD OF USE

BACKGROUND OF THE INVENTION

This invention relates to phosphate derivatives. More particularly, it relates to new phosphate derivatives which have antitumor activity, to a process for preparation thereof, and to a pharmaceutical composition comprising the same for therapeutical treatment of cancer in human beings and animals.

SUMMARY OF THE INVENTION

One object of this invention is to provide new and useful phosphate derivatives.

Another object of this invention is to provide process for preparation of the phosphate derivatives.

A further object of this invention is to provide useful pharmaceutical composition comprising said phosphate derivatives as an antitumor agent.

Still a further object of the present invention is to provide a therapeutical method of treating cancer.

DESCRIPTION OF THE PRIOR ART

The phosphate derivatives of the present invention are novel and include the compounds of the formula [I]:

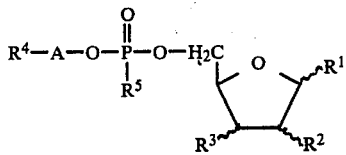

wherein
$R^1$, $R^2$ and $R^3$ are each hydroxy, alkoxy, alkanoylamino or protected hydroxy;
A is lower alkylene;
$R^4$ is alkylammonio, cyclic ammonio or cyclic amino; and
$R^5$ is oxido anion or hydroxy;
and pharmaceutically acceptable salts thereof.

In the above and subsequent description of the present specification, suitable examples and illustrations of the various definitions to be included within the scope of the invention are explained in detail.

The term "lower" is intended to mean 1 to 6 carbon atom(s) and the term "higher" is intended to mean 7 to 25 carbon atoms, unless otherwise indicated.

Suitable "alkoxy" for $R^1$, $R^2$ and $R^3$ is straight or branched one containing 1 to 25 carbon atoms and may include methoxy, ethoxy, propoxy, isopropoxy, butoxy, tert-butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, eicosyloxy, heneicosyloxy, docosyloxy, tricosyloxy, tetracosyloxy, pentacosyloxy and the like.

Suitable "alkanoyl" moiety in the "alkanoylamino" for $R^1$, $R^2$ and $R^3$ is straight or branched one containing 1 to 25 carbon atoms and may include formyl, acetyl, propionyl, butyryl, isobutyryl, valeryl, isovaleryl, pivaloyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, eicosanoyl, heneicosanoyl, docosanoyl, tricasanoyl, tetracosanoyl, pentacosanoyl and the like.

Suitable protective group of the "protected hydroxy" for $R^1$, $R^2$ and $R^3$ is a conventional protective group for hydroxy such as ar(lower)alkyl (e.g. benzyl, p-methoxybenzyl, benzhydryl, trityl, trimethoxytrityl, etc.), lower alkanoyl as mentioned before, substituted lower alkanoyl (e.g. trifluoroacetyl, chloroacetyl, etc.), lower alkoxycarbonyl (e.g. methoxycarbonyl, trichloroethoxycarbonyl, tert-butoxycarbonyl, etc.), aroyl (e.g. benzoyl, toluoyl, xyloyl, naphtoyl, etc.), ar(lower)alkanoyl (e.g. phenylacetyl, phenylpropionyl, phenylbutyryl, etc.), aralkoxycarbonyl (e.g. benzyloxycarbonyl, etc.), and two adjacent hydroxy groups may be protected as a cyclic acetal (e.g. methyleneacetal, ethylideneacetal, benzylideneacetal, isopropylideneacetal, cyclohexylideneacetal, etc.), and the like.

Suitable "lower alkylene" for A is straight or branched one containing 2 to 6 carbon atoms and may include ethylene, trimethylene, propylene, tetramethylene, pentamethylene, hexamethylene and the like.

Suitable "alkylammonio" for $R^4$ may include trialkylammonio such as trimethylammonio, triethylammonio, dimethylethylammonio, diethylmethylammonio, tripropylammonio, dimethylpropylammonio, tributylammonio, tripentylammonio, trihexylammonio, and the like.

Suitable "cyclic ammonio" for $R^4$ may include a 5, 6 or 7-membered heterocyclic ring containing at least one quarterly nitrogen atom such as oxazolio, isoxazolio, thiazolio, isothiazolio, 3H-imidazolio, 2H-imidazolio, 2H-pyrazolio, 2H-1,2,4-triazol-1-io, pyridinio, pyrazinio, pyrimidinio, pyridazinio, 1,2,4-triazin-1-io, 2H-azepinio and the like, among which more preferable one is 6-membered heterocyclic ring, and the most preferable one is pyridinio.

Suitable "cyclic amino" for $R^4$ may include a 5, 6 or 7-membered heterocyclic ring containing at least one tertiary nitrogen atom such as 1-pyrrolyl, 1-pyrrolinyl, 1-pyrrolidinyl, 1-imidazolyl, 1-pyrazolyl, piperidino, morpholino, 1-piperazinyl, 2-imidazolin-1-yl, 2-pyrazolidinyl, 1-homopiperazinyl, homopiperidino, homomorpholino, and the like, among which preferable one is 6 membered heterocyclic ring, and the most preferable one is 1-piperazinyl.

The above cyclic ammonio or cyclic amino group for $R^4$ may be substituted with lower alkyl (e.g. methyl, ethyl, propyl, isopropyl, butyl, isobutyl, sec-butyl, tert-butyl, pentyl, hexyl, etc.).

It is to be noted that the compound having a cyclic amino group for $R^4$ and hydroxy group for $R^5$ may be nomenclated as an intramolecular salt such as a cyclic ammonio, for example, 1-pyrrolio, 1-piperidinio, 4-morpholinio, 1-piperzinio, 1-imidazolinio and the like.

It is to be understood that there may be one or more stereoisomeric mixture such as optical isomer(s) due to asymmetric carbon atom(s) in the molecules, and these isomers are also included within the scope of the present invention. For instance, the compounds [I] include the ones where each substituent $R^1$, $R^2$ and $R^3$ being bonded below or above the plane of the tetrahydrofuran ring of the compounds [I], such as $\alpha$ and $\beta$ isomer of xylofuranose, ribofuranose, arabinofuranose, lyxofuranose and the derivatives thereof.

Suitable pharmaceutically acceptable salts of the object compounds [I] are conventional non-toxic salts and may include an acid addition salt such as an inorganic acid addition salt (e.g., hydrochloride, hydrobromide, sulfate, phosphate, etc.), an organic acid addition salt (e.g., oxalate, maleate, lactate, tartrate, fumarate, methanesulfonate, benzenesulfonate, toluenesulfonate, etc.) or a salt with an amino acid (e.g., arginine aspartic acid, glutamic acid, etc.), a salt with a base such as alkali metal salt (e.g., sodium salt, potassium salt, etc.), and the like.

The object compounds (I) of the present invention can be prepared by the following process.

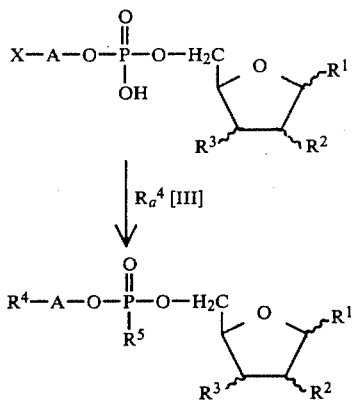

wherein
$R^1$, $R^2$, $R^3$, A, $R^4$ and $R^5$ are each as defined above,
X is an acid residue, and
$R_a^4$ is alkylamine or cyclic amine.

That is, the object compounds [I] and salts thereof can be prepared by reacting a compound [II] or its salt with an amine compound [III] or its salt.

Suitable "acid residue" for X may include halogen (e.g. fluorine, chlorine, bromine, iodine), acyloxy (e.g. benzenesulfonyloxy, tosyloxy, etc.), and the like.

Suitable "alkylamine or cyclic amine" for $R_a^4$ is the one corresponding to alkylammonio, cyclic ammonio or cyclic amine for $R^4$ as illustrated before.

Suitable salt of the compound [II] is an alkali metal salt as exemplified before for the compound [I].

Suitable salt of the compound [III] is an acid addition salt as exemplified before for the compound [I].

The reaction is usually carried out in a solvent such as acetone, methanol, tetrahydrofuran, chloroform, benzene or any other solvent which does not adversely affect the reaction. In case that the compound [III] or its salt is liquid, it can also be used as a solvent.

The reaction temperature is not critical and the reaction is preferably carried out under warming or heating.

The object compound [I] may occasionally be obtained as a salt with the acid residue (X⁻ anion).

The above salt can optionally be transformed to another salt or the corresponding intramolecular salt by a conventional method, such as treatment with an ion-exchange resin, or treatment with silver ion.

Some of the starting compounds [II] and their salts are novel and they can be prepared by the methods as shown in the Examples or the methods chemically equivalent thereto.

The following pharmacological test data show that the object compounds [I] of the present invention exhibit high anti-tumor activity.

Test Method

Groups of eight female BALB/c mice, aged 8–9 weeks and weighing 18.0–22.5 g were used.

Fibrosarcoma Meth A (hereinafter referred to as Meth A) was successively transferred every 7 days into BALB/c mice by intraperitoneal inoculation of the ascites cells thereof and the Meth A in the ascites cells as harvested 6 or 7 days after the inoculation was used as tumor cells.

Each of the BALB/c mice was inoculated intrapleurally with $5 \times 10^5$ Meth A cells in 0.1 ml Hanks solution.

Test compound was dissolved in phosphate buffer saline solution, and was injected into pleural cavity to each of the mice in doses of 100 μg/0.5 ml/mouse three times, i.e. before 14 days, after 1 hour and after 3 days of tumor implantation.

The control group was given with a vehicle alone in the same way.

The antitumor activity of the test compound was estimated by comparing mean survival time of the two groups.

T: Mean survival time of the medicated group
C: Mean survival time of the control group Test Compound Ex 4-(3)

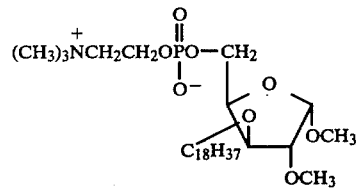

Ex 6-(7)

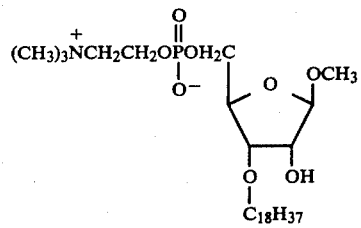

Control Compound (rac)-1-O-Octadecyl-2-O-methyl-glycerol-3-phosphorylcholine which is described in British Pat. No. 1,583,661.

Test Results

| Compounds | Anti-tumor activity *a (%) |
|---|---|
| Ex 4 - (3) | 408 |
| Ex 6 - (7) | 383 |
| Control Compound | 302.8 |

*a: T/C × 100

As being apparent from the above test results, the object compound [I] of the present invention is useful as an antitumor agent.

The effective ingredient may usually be administered with a dose of 0.1 mg/kg to 500 mg/kg, 1 to 4 times a day in a preparations such as tablet, granule, powder, capsule, syrup, injection, suppository and the like. However, the above dosage may be increased or decreased according to the age, weight or conditions of a patient or the administering method.

The above mentioned pharmaceutical preparations can be prepared in a conventional manner by using conventional carriers and additives.

The present invention is illustrated by the following Examples in more detail.

EXAMPLE 1

(1) A mixture of methyl 2-O-methyl-$\beta$-D-xylofuranoside (3.45 g), trityl chloride (5.85 g), triethylamine (5 ml), and 4-dimethylaminopyridine (0.2 g) in dry N,N-dimethylformamide (15 ml) was stirred for 10 hours at ambient temperature.

The resulting mixture was poured into water (200 ml) and extracted with diethyl ether. The combined extracts were washed with water, dried, and evaporated under reduced pressure.

The oily residue was purified by column chromatography on silica gel (100 g, elution by benzene and then chloroform) to give 4.90 g of methyl 2-O-methyl-5-O-trityl-$\alpha,\beta$-D-xylofuranoside as an oil.

IR (film): 3500, 3050, 2900, 2800, 1595, 1490, 1445 cm$^{-1}$.

(2) To a solution of the above compound (4.80 g) in dry N,N-dimethylformamide (24 ml) was added sodium hydride (0.82 g, 50% oil dispersion) in one portion. After the mixture was stirred for one hour at ambient temperature, a solution of 1-bromooctadecane (4.18 g) in dry N,N-dimethylformamide (12 ml) was added dropwise thereto. The resulting mixture was stirred for 24 hours at ambient temperature and then poured into ice water (200 ml). The separated oil was extracted with diethyl ether.

The combined extracts were washed with water, dried, and evaporated under reduced pressure. The residue was purified by column chromatography on silica gel (160 g, elution by benzene and then benzene/chloroform=4$^v$/1$^v$) to yield 3.3 g of methyl 2-O-methyl-3-O-octadecyl-5-O-trityl-$\beta$-D-xylofranoside as a colorless oil and 2.76 g of the $\alpha$-isomer as a colorless oil.

$\beta$-isomer
IR (film): 3050, 3000, 1595, 1490, 1460, 1450 cm$^{-1}$.
$\alpha$-isomer:
IR (film): 2930, 2850, 1460, 1445 cm$^{-1}$.

(3) To a solution of methyl 2-O-methyl-3-O-octadecyl-5-O-trityl-$\beta$-D-xylofuranoside (3.2 g) in dry methylene chloride (32 ml) was added trifluoroacetic acid (3.2 ml) in one portion at ambient temperature. After stirring for 1.5 hours at the same temperature, the yellow solution was washed with water, aqueous sodium bicarbonate and water succesively, dried, and evaporated under reduced pressure. The residue was triturated in n-hexane to remove triphenylcarbinol by filtration. The filtrate was evaporated and then the residue was purified by column chromatography on silica gel (40 g, elution by chloroform) to yield 1.21 g of methyl 2-O-methyl-3-O-octadecyl-$\beta$-D-xylofuranoside as a thick oil.

IR (film): 3500, 2910, 2850, 1465 cm$^{-1}$.

(4) To a mixture of the above compound (1.15 g) and triethylamine (0.56 g) in dry methylene chloride (5 ml) was dropwise added a solution of 2-bromoethylphosphorodichloridate (1.33 g) in dry methylene chloride (2 ml) over a period of 10 minutes at 5° C. After the addition was complete, the mixture was stirred for 8 hours at ambient temperature and then cooled in an ice bath. To the cold solution was added dropwise a mixture of pyridine (3 ml) and water (1.5 ml) over a period of 2 minutes. The ice bath was removed and the mixture was stirred for one hour at ambient temperature to hydrolyze phosphorochloridate derivative and then evaporated to dryness. The residue was dissolved in a mixture of ethyl acetate (25 ml) and diethyl ether (25 ml). The solution was washed with 10% aqueous hydrochloric acid and brine, dried, and evaporated to yield 1.8 g of methyl 2-O-methyl-3-O-octadecyl-$\beta$-D-xylofuranoside 5-(2-bromoethyl phosphate) as a waxy solid.

IR (Nujol): 1460, 1375, 1260 cm$^{-1}$.
NMR (CDCl$_3$) ppm: 0.86 (m, 3H), 1.27 (s, 32H), 3.42 (s, 6H), 3.50 (m, 4H), 3.72 (m, 1H), 3.90 (dd, 1H, J=8, 2.5 Hz), 4.36 (m, 5H), 4.86 (s, 1H).

(5) A mixture of the above compound (1.7 g) and 30% aqueous trimethylamine (5.4 g) in methanol (11 ml) was stirred at 50° C. for 7.5 hours. An insoluble material was filtered off and the filtrate was evaporated under reduced pressure. The residue was dissolved in 90% aqueous methanol (17 ml) and treated with silver acetate (1.13 g) for 1.5 hours with vigorous stirring. The precipitates were removed by filtration and washed with methanol. The combined filtrate and washings were evaporated to dryness. The resulting solid was chromatographed on silica gel (35 g, elution by CHCl$_3$:CH$_3$OH:H$_2$O=65:25:2) to give 1.0 g of methyl 2-O-methyl-3-O-octadecyl-$\beta$-D-xylofuranoside 5-(choline phosphate) which was purified by recrystallization from chloroform-acetone.

mp. 200° C. (dec.)
IR (Nujol): 3400, 1460, 1375, 1250 cm$^{-1}$.
NMR (CDCl$_3$) ppm: 0.90 (m, 3H), 1.28 (s, 32H), 3.33 (s, 6H), 3.35 (m, 2H), 3.40 (s, 9H), 3.68 (m, 1H), 3.84 (m, 3H), 4.10 (m, 1H), 4.36 (m, 4H), 4.82 (s, 1H).
Anal. Calcd. for C$_{30}$H$_{62}$NO$_8$P.2H$_2$O, C; 57.03, H; 10.53, N; 2.22.
Found, C; 56.15; H; 10.60, N; 2.18.

EXAMPLE 2

Methyl 2-O-methyl-3-O-octadecyl-$\beta$-D-xylofuranoside 5-[2-(1-pyridinio)ethyl phosphate] (0.75 g) was obtained by reacting methyl 2-O-methyl-3-O-octadecyl-$\beta$-D-xylofuranoside 5-(2-bromoethyl phosphate) (2.0 g) with pyridine (5 ml) in a similar manner to that of Example 1-(5).

mp. 110° C. (dec.).
IR (Nujol): 3360, 1640, 1495, 1250 cm$^{-1}$.
NMR (CD$_3$OD) ppm: 0.90 (m, 3H), 1.30 (m, 32H), 3.37 (s, 3H), 4.00 (s, 3H), 3.1~4.1 (m, 6H), 4.2~4.5 (m, 3H), 4.78~5.00 (m, 3H), 8.00~9.1 (m, 5H).
Anal. Calcd. for C$_{32}$H$_{58}$NO$_8$P.H$_2$O, C; 60.64, H; 9.54, N; 2.21.
Found, C; 60.94, H; 9.31, N; 2.19.

EXAMPLE 3

Methyl 2-O-methyl-3-O-octadecyl-$\beta$-D-xylofuranoside 5-[2-(4-methyl-1-piperazinyl)ethyl phosphate] (1.69 g) was obtained as an oil by reacting methyl 2-O-methyl-3-O-octadecyl-$\beta$-D-xylofuranoside 5-(2-bromoethyl phosphate) (3.75 g) with 1-methylpiperazine (6.1 ml) in a similar manner to that of Example 1-(5).

IR (film): 3370, 2400, 1650, 1460, 1215 cm$^{-1}$.
NMR (CDCl$_3$) ppm: 0.9 (m, 3H), 1.3 (m, 32H), 2.60 (s, 3H), 2.7~4.6 (m, 20H), 3.42 (s, 6H), 4.82 (s, 1H).

Anal. Calcd. for $C_{32}H_{65}N_2O_8P \cdot H_2O$, C; 58.69, H; 10.31, N; 4.28.

Found, C; 58.99, H; 10.05, N; 4.34.

EXAMPLE 4

(1) Methyl 2-O-methyl-3-O-octadecyl-α-D-xylofuranoside (1.70 g) was obtained from methyl 2-O-methyl-3-O-octadecyl-5-O-trityl-α-D-xylofuranoside (3.89 g) in a similar manner to that of Example 1-(3).

mp. 65.5° to 66.5° C.

IR (Nujol): 3250, 3100, 1130 cm$^{-1}$.

(2) Methyl 2-O-methyl-3-O-octadecyl-α-D-xylofuranoside 5-(2-bromoethyl phosphate) (2.07 g) was obtained as a waxy solid from the above compound (1.50 g) in a similar manner to that of Example 1-(4).

IR (Nujol): 1120, 1070, 1010 cm$^{-1}$.

(3) Methyl 2-O-methyl-3-O-octadecyl-α-D-xylofuranoside 5-(choline phosphate) (1.65 g) was obtained by reacting the above compound (2.04 g) with 30% aqueous trimethylamine (6.49 g) in a similar manner to that of Example 1-(5).

mp. 207° C. (dec.).

IR (Nujol): 3550, 3400, 3320, 1240, 1060 cm$^{-1}$.

NMR (CDCl$_3$) ppm: 0.88 (m, 3H), 1.28 (m, 32H), 3.2~3.6 (m, 15H), 3.6~4.5 (m, 11H), 4.92 (d, 1H, J=4 Hz).

Anal. Calcd. for $C_{30}H_{62}NO_8P \cdot 2H_2O$, C; 57.03, H; 10.53, N; 2.22.

Found, C; 57.60, H; 10.32, N; 2.22.

EXAMPLE 5

(1) 1,2-O-Isopropylidene-3-O-octadecyl-5-O-trityl-α-D-xylofuranose (22.55 g) was obtained as an oil from 1,2-O-isopropylidene-5-O-trityl-α-D-xylofuranose (21.6 g) in a similar manner to that of Example 1-(2).

IR (film): 3050, 3025, 2920, 2850, 1595, 1490, 1445, 1370 cm$^{-1}$.

(2) 1,2-O-Isopropylidene-3-O-octadecyl-α-D-xylofuranose (12.7 g) was obtained as a waxy solid from the above compound (22.5 g) in a similar manner to that of Example 1-(3).

IR (Nujol): 3500, 1460, 1375, 1080, 1005 cm$^{-1}$.

(3) 1,2-O-Isopropylidene-3-O-octadecyl-α-D-xylofuranose 5-(2-bromoethyl phosphate) (6.36 g) was obtained as an oil from the above obtained compound (4.42 g) in a similar manner to that of Example 1-(4).

IR (film): 2910, 2850, 1460 cm$^{-1}$.

(4) 1,2-O-Isopropylidene-3-O-octadecyl-α-D-xylofuranose 5-(choline phosphate) (3.37 g) was obtained from the above compound (6.25 g) in a similar manner to that of Example 1-(5).

mp. 217° to 218° C.

IR (Nujol): 3300, 1470, 1380, 1240, 1090, 1060, 1015 cm$^{-1}$.

NMR (CDCl$_3$) ppm: 0.87 (m, 3H), 1.24 (s, 3H), 1.28 (s, 32H), 1.45 (s, 3H), 3.37 (s, 9H), 3.4~4.4 (m, 10H), 4.48 (d, 1H, J=4 Hz), 5.89 (d, 1H, J=4 Hz).

Anal. Calcd. for $C_{31}H_{62}NO_8P \cdot 2H_2O$, C; 57.83, H; 10.33, N; 2.18.

Found, C; 57.21, H; 10.45, N; 2.13.

EXAMPLE 6

(1) 1,2:5,6-Di-O-cyclohexylidene-3-O-octadecyl-α-D-allofuranose (30.3 g) was obtained from 1,2:5,6-di-O-cyclohexylidene-α-D-allofuranose (23.8 g) in a similar manner to that of Example 1-(2).

mp. 43° to 44° C.

IR (film): 2910, 2850, 1470, 1450, 1365 cm$^{-1}$.

(2) A solution of the above compound (10.0 g) in a mixture of acetic acid (200 ml) and water (60 ml) was heated at 60° C. for 4.5 hours. The solvents were evaporated below 40° C. under reduced pressure. The residue was purified by column chromatography on silicagel (150 g, elution by benzene and then benzene:acetone=10:1). The eluates containing the object compound were combined and concentrated to give 7.53 g of 1,2-O-cyclohexylidene-3-O-octadecyl-α-D-allofuranose as an oil.

IR (film): 3400, 2910, 2850, 1460, 1445 cm$^{-1}$.

(3) To a stirred solution of the above compound (7.45 g) in tetrahydrofurane (300 ml) was added a solution of periodic acid (7.84 g) in water (45 ml) in one portion at ambient temperature.

The stirring was continued for 1.5 hours at the same temperature. The solvents were evaporated to dryness. The residue was extracted with diethyl ether.

The extracts were washed successively with water, an aqueous sodium bicarbonate solution and brine, dried and evaporated to give 7.25 g of crude product. The product was purified by column chromatography on silica gel (70 g, elution by benzene, benzene:chloroform=1:1, and then chloroform) to yield 6.81 g of 1,2-O-cyclohexylidene-3-O-octadecyl-α-D-ribo-pentodialdo-1,4-furanose as an oil.

IR (film): 3450, 2920, 2850, 1735 cm$^{-1}$.

(4) To a stirred solution of the above compound (5.5 g) in a mixture of methanol (27 ml) and tetrahydrofurane (27 ml) was added sodium borohydride (0.6 g) in one portion at ambient temperature. After the mixture was stirred for 10 minutes at the same temperature, the excess of sodium borohydride was decomposed by the addition of 10% aqueous hydrochloric acid. The solvents were evaporated under reduced pressure and the residue was extracted with chloroform. The extracts were combined and washed with water, an aqueous sodium bicarbonate solution, and brine successively, dried, and evaporated to dryness to yield 5.6 g of 1,2-O-cyclohexylidene-3-O-octadecyl-α-D-ribofuranose as a crystal.

mp. 35° to 37° C.

IR (Nujol): 3400, 3300, 1455, 1375 cm$^{-1}$.

(5) 1,2-O-Cyclohexylidene-3-O-octadecyl-α-D-ribofuranose 5-(2-bromoethyl phosphate) (5.29 g) was obtained as an oil from the above compound (5.5 g) in a similar manner to that of Example 1-(4).

IR (film): 3450, 1460, 1455 cm$^{-1}$.

(6) To a solution of the above compound (4.5 g) in a mixture of dry methanol (45 ml) and dry tetrahydrofuran (45 ml) was added conc. sulfuric acid (1.35 g) in one portion. The mixture was refluxed for 3 hours and then allowed to cool to ambient temperature. Barium carbonate (9.0 g) was added thereto. The resultant suspension was stirred for one hour at ambient temperature and then filtered off. The filtrate was evaporated to give 5.0 g of crude product, which was purified by column chromatography on silica gel (100 g, elution by chloroform and then 1~10% methanol in chloroform) to yield 3.85 g of methyl 3-O-octadecyl-β-D-ribofuranoside 5-(2-bromoethyl phosphate) as a waxy solid.

IR (Nujol): 3420, 1470, 1225 cm$^{-1}$.

(7) Methyl 3-O-octadecyl-β-D-ribofuranoside 5-(choline phosphate) (3.0 g) was obtained from the above compound (3.7 g) in a similar manner to that of Example 1-(5).

mp. 140° C.

IR (Nujol): 3400, 3200, 1460, 1245 cm$^{-1}$.

NMR (CDCl$_3$) ppm: 0.86 (m, 3H), 1.28 (s, 32H), 3.2~4.5 (m, 23H), 4.88 (s, 1H).

Anal. Calcd. for C$_{29}$H$_{60}$NO$_8$P.H$_2$O, C; 58.06, H; 10.42, N; 2.33.

Found, C; 57.70, H; 10.68, N; 2.33.

EXAMPLE 7

(1) To a stirred mixture of 1,2-O-isopropylidene-3-amino-3-deoxy-α-D-ribofuranose (3.8 g) and triethylamine (4 ml) in dry benzene (38 ml) was dropwise added, a solution of octadecanoyl chloride (6.08 g) in dry benzene (10 ml) over a period of one hour in an ice bath. After stirring for 3 hours at ambient temperature, the mixture was washed successively with water, an aqueous sodium hydroxide solution, and water, dried, and evaporated to give crude product (8.28 g), which was purified by column chromatography on silica gel (160 g, elution by chloroform and then 1% methanol in chloroform) to yield 3.29 g of 1,2-O-isopropylidene-3-octadecanoylamino-3-deoxy-α-D-ribofuranose as a crystal.

mp. 74° to 76° C.

IR (Nujol): 3350, 1650, 1530, 1460, 1380, 1255, 1205 cm$^{-1}$.

(2) 1,2-O-Isopropylidene-3-octadecanoylamino-3-deoxy-α-D-ribofuranose 5-(2-bromoethyl phosphate) (3.21 g) was obtained as a waxy solid from the above compound (3.2 g) in a similar manner to that of Example 1-(4).

IR (Nujol): 3300, 1645, 1540, 1460, 1380, 1255 cm$^{-1}$.

(3) 1,2-O-Isopropylidene-3-octadecanoylamino-3-deoxy-α-D-ribofuranose 5-(choline phosphate) (1.90 g) was obtained from the above compound (2.6 g) in a similar manner to that of Example 1-(5).

mp. 211° to 218° C. (dec.).

IR (Nujol): 3300, 1645, 1560, 1460, 1375, 1245 cm$^{-1}$.

NMR (CDCl$_3$) ppm: 0.86 (m, 3H), 1.27 (m, 33H), 1.51 (s, 3H), 2.20 (m, 2H), 3.36 (s, 9H), 3.6~4.4 (m, 8H), 4.60 (m, 1H), 5.82 (d, 1H, J=4 Hz), 6.44 (m, 1H).

Anal. Calcd. for C$_{31}$H$_{61}$N$_2$O$_8$P.3/2H$_2$O, C; 57.47, H; 9.96, N; 4.32.

Found, C; 57.82, H; 10.21, N; 4.34.

EXAMPLE 8

(1) Methyl 3,5-di-O-benzyl-2-O-octadecyl-β-D-xylofuranoside (6.1 g) was obtained as an oil from methyl 3,5-di-O-benzyl-β-D-xylofuranoside (6.0 g) in a similar manner to that of Example 1-(2).

IR (film): 3010, 2900, 2850, 1450, 1110, 1060 cm$^{-1}$.

(2) A solution of the above obtained compound (6.0 g) in a mixture of methanol (120 ml), tetrahydrofurane (60 ml), and acetic acid (36 ml) containing palladium on charcoal (10%, 3.0 g) was hydrogenated at 4 atm hydrogen pressure for 24 hours. The catalyst was removed by filtration followed by washing with chloroform. The combined filtrate and washings were evaporated under reduced pressure to yield 4.5 g of crude methyl 2-O-octadecyl-α,β-D-xylofuranoside as a waxy solid, which was used in the following step without further purification.

IR (Nujol): 3370, 1465, 1375, 1110, 1045 cm$^{-1}$.

(3) Methyl 2-O-octadecyl-5-O-trityl-β-D-xylofuranoside (3.95 g) was obtained as an oil from the above compound (4.44 g) in a similar manner to that of Example 1-(1).

IR (film): 3500, 3050, 3010, 2910, 2840, 1595, 1490, 1465, 1445 cm$^{-1}$.

(4) A mixture of the above compound (3.9 g), acetic anhydride (2 ml) and dry pyridine (4 ml) was heated at 80° C. for 2 hours. The resultant mixture was poured into water (20 ml) and the separated oil was extracted with diethyl ether. The extract was washed with 5% aqueous hydrochloric acid, water, aqueous sodium bicarbonate, water, and brine successively. After drying, the solvent was evaporated to give 4.1 g of methyl 3-O-acetyl-2-O-octadecyl-5-O-trityl-β-D-xylofuranoside as an oil.

IR (film): 3050, 3010, 2900, 2830, 1740, 1235 cm$^{-1}$.

(5) Methyl 3-O-acetyl-2-O-octadecyl-β-D-xylofuranoside (1.67 g) was obtained as a waxy solid from the above obtained compound (4.0 g) in a similar manner to that of Example 1-(3).

IR (Nujol): 3430, 1740, 1710, 1460, 1375, 1110, 1065 cm$^{-1}$.

(6) Methyl 3-O-acetyl-2-O-octadecyl-β-D-xylofuranoside 5-(2-bromoethyl phosphate) (2.22 g) was obtained as an oil from the above compound (1.6 g) in a similar manner to that of Example 1-(4).

IR (film): 2900, 2850, 1740 cm$^{-1}$.

(7) A mixture of the above compound (2.15 g) and 30% aqueous trimethylamine (6.6 g) in methanol (13 ml) was stirred at 50° C. for 9 hours. An insoluble material was filtered off and the filtrate was evaporated under reduced pressure. The residue was dissolved in methanol (50 ml). To the solution was added 28% methanolic sodium methoxide (2 ml) and the mixture was stirred for 6 hours at ambient temperature. The mixture was evaporated and the residue was dissolved in a mixture of methanol (10 ml), chloroform (5 ml), and water (5 ml). The solution was adjusted to pH 2 with 10% hydrochloric acid and passed through a mixed ion-exchange column, containing Amberlite IRC-50 (H+) (40 ml) and IR-45 (OH−) (40 ml). The eluates were evaporated to dryness to give 2.1 g of crude product, which was further purified by column chromatography on silica gel (42 g) (elution by CHCl$_3$:CH$_3$OH:H$_2$O=65:25:4) and recrystallization from chloroform-acetone to give 0.33 g of methyl 2-O-octadecyl-β-D-xylofuranoside 5-(choline phosphate).

mp. 217° to 220° C.

IR (Nujol): 3200, 1460, 1200, 1045 cm$^1$.

NMR (CDCl$_3$) ppm: 0.87 (m, 3H) 1.25 (s, 32H), 3.23 (s, 9H), 3.35 (s, 3H), 3.2~4.6 (m, 11H), 4.73 (s, 1H).

Anal. Calcd. for C$_{29}$H$_{60}$NO$_8$P.5/2H$_2$O C; 55.57, H; 10.45, N; 2.23.

Found, C; 55.43, H; 10.33, N; 2.07.

EXAMPLE 9

(2) To a solution of 5-O-benzyl-1,2-O-isopropylidene-3-O-methyl-α-D-xylofuranose (7.0 g) in methanol (21 ml) was added conc. hydrochloric acid (0.2 ml). The mixture was refluxed for 2 hours and then allowed to cool to ambient temperature. To the resultant mixture was added barium carbonate (2.0 g). The suspension was stirred for 2 hours and filtered off. The filtrate was evaporated under reduced pressure. The oily residue was purified by column chromatography on silica gel (150 g, elution by CHCl$_3$, 1~3% CHCl$_3$ in methanol) to give 2.4 g of methyl 5-O-benzyl-3-O-methyl-α-D-xylofuranoside and 3.25 g of methyl 5-O-benzyl-3-O-methyl-β-D-xylofuranoside. α-isomer, oil NMR (CCl$_4$) ppm: 2.44 (d, 1H, J=7 Hz), 3.36 (s, 3H), 3.44 (s, 3H), 3.58 (m, 3H), 3.98 (m, 1H), 4.18 (m, 1H), 4.45 (s, 2H), 4.79 (d, 1H, J=5 Hz), 7.21 (m, 5H). β-isomer, oil NMR (CCl$_4$) ppm: 2.48 (brs, 1H), 3.26 (s, 3H), 3.30 (s, 3H), 3.52 (m, 3H), 3.98 (m, 1H), 3.94 (m, 1H), 4.48 (s, 2H), 4.63 (s, 1H), 7.21 (m, 5H).

(2) Methyl 5-O-benzyl-3-O-methyl-2-O-octadecyl-$\alpha,\beta$-D-xylofuranoside (9.5 g) was obtained as an oil from the mixture of above $\alpha$ and $\beta$ isomer (5.9 g) in a similar manner to that of Example 1-(2).

IR (film): 2900, 1820, 1460, 1360, 1110 cm$^{-1}$.

(3) Methyl 3-O-methyl-2-O-octadecyl-$\alpha,\beta$-D-xylofuranoside (3.92 g) was obtained from the above compound (9.4 g) in a similar manner to that of Example 8-(2).

IR (film): 3350, 1460, 1375, 1120, 1065 cm$^{-1}$.

(4) Methyl 3-O-methyl-2-O-octadecyl-$\alpha,\beta$-D-xylofuranoside 5-(2-bromoethyl phosphate) (5.15 g) was obtained as an oil from the above compound (3.80 g) in a similar manner to that of Example 1-(4).

IR (film): 2900, 2840, 1460 cm$^{-1}$.

(5) Methyl 3-O-methyl-2-O-octadecyl-$\alpha,\beta$-D-xylofuranoside 5-(choline phosphate) (3.42 g) was obtained from the above compound (5.0 g) in a similar manner to that of Example 1-(5).

mp. 220° C.

IR (Nujol): 3350, 1645, 1460, 1375 cm$^{-1}$.

NMR (CDCl$_3$) ppm: 0.87 (m, 3H), 1.28 (s, 32H), 3.3~4.5 (m, 26H), 4.80~4.92 (m, 1H).

Anal. Calcd. for C$_{30}$H$_{62}$NO$_8$P.2H$_2$O, C; 57.03, H; 10.53, N; 2.22.

Found, C; 57.00, H; 10.60, N; 2.16.

What is claimed is:

1. A compound of the formula:

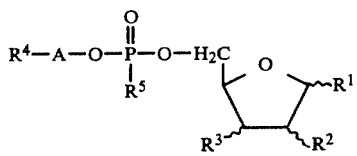

wherein
R$^1$, R$^2$, and R$^3$ are each hydroxy, alkoxy, alkanoylamino or protected hydroxy;
A is lower alkylene;
R$^4$ is alkylammonio, cyclic ammonio or cyclic amino; and
R$^5$ is oxido anion or hydroxy;

or a pharmaceutically acceptable salt thereof.

2. The compound of claim 1, wherein R$^1$, R$^2$ and R$^3$ are each alkoxy.

3. The compound of claim 2, wherein R$^4$ is alkylammonio.

4. The compound of claim 3, which is methyl 2-O-methyl-3-O-octadecyl-$\beta$-D-xylofuranoside 5-(choline phosphate).

5. The compound of claim 3, which is methyl 2-O-methyl-3-O-octadecyl-$\alpha$-D-xylofuranoside 5-(choline phosphate).

6. The compound of claim 3, which is methyl 3-O-methyl-2-O-octadecyl-$\alpha,\beta$-D-xylofuranoside 5-(choline phosphate).

7. The compound of claim 2, wherein R$^4$ is cyclic ammonio.

8. The compound of claim 7, which is methyl 2-O-methyl-3-O-octadecyl-$\beta$-D-xylofuranoside 5-[2-(1-pyridinio)ethyl phosphate].

9. The compound of claim 2, wherein R$^4$ is cyclic amino.

10. The compound of claim 9, which is methyl 2-O-methyl-3-O-octadecyl-$\beta$-D-xylofuranoside 5-[2-(4-methyl-1-piperazinyl)ethyl phosphate].

11. The compound of claim 1, wherein R$^1$ and R$^3$ are each alkoxy, R$^2$ is hydroxy and R$^4$ is alkylammonio.

12. The compound of claim 11, which is methyl 3-O-octadecyl-$\beta$-D-ribofuranoside 5-(choline phosphate).

13. The compound of claim 1, wherein R$^1$ and R$^2$ are each alkoxy, R$^3$ is hydroxy and R$^4$ is alkylammonio.

14. The compound of claim 13, which is methyl 2-O-octadecyl-$\beta$-D-xylofuranoside 5-(choline phosphate).

15. The compound of claim 1, wherein R$^1$ and R$^2$ are each protected hydroxy, and R$^4$ is alkylammonio.

16. The compound of claim 15, wherein R$^3$ is alkoxy.

17. The compound of claim 15, wherein R$^3$ is alkanoylamino.

18. A pharmaceutical composition for treating fibrosarcoma Meth A comprising:
(a) a pharmaceutically effective amount of the compound of claim 1 and
(b) a pharmaceutically acceptable carrier or excipient.

19. A method for treating fibrosarcoma Meth A which comprises administering a pharmaceutically effective amount of the compound of claim 1 to a subject in need of said treatment.

* * * * *